United States Patent
Higuchi et al.

(10) Patent No.: US 9,630,904 B2
(45) Date of Patent: Apr. 25, 2017

(54) CATALYST FOR USE IN PRODUCTION OF METHYL METHACRYLATE, AND METHOD FOR PRODUCING METHYL METHACRYLATE

(71) Applicant: MITSUBISHI GAS CHEMICAL COMPANY, INC., Tokyo (JP)

(72) Inventors: Katsumi Higuchi, Tokyo (JP); Saori Hirokawa, Niigata (JP); Yuuichi Sugano, Niigata (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 15/106,497

(22) PCT Filed: Dec. 22, 2014

(86) PCT No.: PCT/JP2014/083816
§ 371 (c)(1),
(2) Date: Jun. 20, 2016

(87) PCT Pub. No.: WO2015/098786
PCT Pub. Date: Jul. 2, 2015

(65) Prior Publication Data
US 2016/0368851 A1    Dec. 22, 2016

(30) Foreign Application Priority Data

Dec. 24, 2013  (JP) ................. 2013-265929

(51) Int. Cl.
*C07C 67/327*   (2006.01)
*B01J 29/08*    (2006.01)

(52) U.S. Cl.
CPC ............. *C07C 67/327* (2013.01); *B01J 29/08* (2013.01); *B01J 2229/42* (2013.01)

(58) Field of Classification Search
CPC ...... C07C 67/327; B01J 29/08; B01J 2229/42
See application file for complete search history.

(56) References Cited

U.S. PATENT DOCUMENTS

| | | | |
|---|---|---|---|
| 5,068,399 A | 11/1991 | Naito et al. | |
| 5,371,273 A | 12/1994 | Shima et al. | |
| 5,739,379 A | 4/1998 | Shima et al. | |
| 7,208,446 B2* | 4/2007 | Stamires | B01J 21/04 423/275 |
| 2010/0189595 A1* | 7/2010 | Webster | A61L 9/014 422/4 |
| 2010/0331571 A1 | 12/2010 | Saito et al. | |

FOREIGN PATENT DOCUMENTS

| | | |
|---|---|---|
| EP | 0 379 691 | 8/1990 |
| EP | 1 658 895 | 5/2006 |
| JP | 63-66146 | 3/1988 |
| JP | 1-290647 | 11/1989 |
| JP | 2-196753 | 8/1990 |
| JP | 3-167155 | 7/1991 |
| JP | 3-167156 | 7/1991 |
| JP | 3-167157 | 7/1991 |
| JP | 6-157413 | 6/1994 |
| JP | 8-188555 | 7/1996 |
| JP | 2009-67808 | 4/2009 |
| JP | 2011-140210 | 7/2011 |

OTHER PUBLICATIONS

International Search Report issued in Japanese Patent Application No. PCT/JP2014/083816, dated Feb. 24, 2015.

* cited by examiner

*Primary Examiner* — Shailendra Kumar
(74) *Attorney, Agent, or Firm* — Greenblum & Bernstein, P.L.C.

(57) ABSTRACT

According to the present invention, a molded catalyst for use in the production of methyl methacrylate can be provided. The molded catalyst comprises synthetic faujasite-type zeolite and a layered magnesium silicate compound, wherein the sulfur content in the layered magnesium silicate compound is 0.10% by weight or less. According to the present invention, a method for producing methyl methacrylate can also be provided. The method is characterized by comprising a step of carrying out a gas-phase catalytic reaction of methyl α-hydroxyisobutyrate using the above-mentioned molded catalyst for use in the production of methyl methacrylate.

6 Claims, No Drawings

CATALYST FOR USE IN PRODUCTION OF METHYL METHACRYLATE, AND METHOD FOR PRODUCING METHYL METHACRYLATE

This application is a 371 of PCT/JP2014/083816, filed on Dec. 22, 2014.

TECHNICAL FIELD

The present invention relates to a catalyst for producing methyl methacrylate by means of a gas-phase catalytic reaction using methyl α-hydroxyisobutyrate as a raw material, a method for producing the catalyst and a method for producing methyl methacrylate using the catalyst. Methyl methacrylate has industrially important uses such as a raw material of polymethyl methacrylate, which is excellent in weather resistance and transparency, and a raw material of various methacrylic acid esters.

BACKGROUND ART

The method for producing methyl methacrylate by means of a gas-phase catalytic reaction using methyl α-hydroxyisobutyrate as a raw material is publicly known. For example, Patent Document 1 discloses a method for producing an α,β-unsaturated carboxylic acid ester in which α-hydroxycarboxylic acid ester, α-alkoxycarboxylic acid ester and β-alkoxycarboxylic acid ester are used solely or in combination as a raw material to carry out a dehydration or dealcoholization reaction with a crystalline alumino silicate as a catalyst. Regarding the crystalline alumino silicate to be used in the production method, the document describes that X-type or Y-type zeolite exhibits particularly excellent catalytic activity. Further, Patent Documents 2, 3 and 4 disclose that a crystalline alumino silicate modified with an alkali metal and/or a platinum group element, in particular, X-type or Y-type zeolite is effective as a catalyst for the production method.

In the case of producing methyl methacrylate from methyl α-hydroxyisobutyrate by means of a gas-phase catalytic reaction using such a crystalline alumino silicate as a catalyst, it is known that there are problems such as temporal deterioration of the catalyst, which is caused because a high boiling point byproduct covers pore inlets of the crystalline alumino silicate, and coloring of a reaction solution due to by-produced diacetyl.

Regarding these problems, Patent Document 5 discloses that when a transition-type synthetic faujasite-type zeolite having a lattice constant in the boundary region between X type and Y type and a defined Na content is used, the production of diacetyl that is a coloring substance can be suppressed, and at the same time, the by-production of the high boiling point byproduct can be reduced to maintain the catalytic activity for a long period of time. In this regard, the document describes that a clay having an aluminium content of less than 5 wt %, in particular, a silica magnesia-based clay is preferably used as a binder for suppressing the by-production of diacetyl.

In addition, Patent Document 6 discloses that when using a catalyst containing, as an active component, a synthetic faujasite-type zeolite with the amount of free alkali being adjusted to 0.1 milliequivalent/g or less, or a molded catalyst obtained by using a synthetic faujasite-type zeolite and a clay whose pH is less than 9 when it is dispersed in water, the by-production of a high boiling point byproduct that causes temporal deterioration of the catalyst is suppressed, and the catalyst life becomes longer.

PRIOR ART DOCUMENTS

Patent Documents

Patent Document 1: Japanese Laid-Open Patent Publication No. H02-196753
Patent Document 2: Japanese Laid-Open Patent Publication No. H03-167155
Patent Document 3: Japanese Laid-Open Patent Publication No. H03-167156
Patent Document 4: Japanese Laid-Open Patent Publication No. H03-167157
Patent Document 5: Japanese Laid-Open Patent Publication No. H06-157413
Patent Document 6: Japanese Laid-Open Patent Publication No. H08-188555

SUMMARY OF THE INVENTION

Problems to be Solved by the Invention

In the aforementioned Patent Document 5 and Patent Document 6, when producing methyl methacrylate by means of a gas-phase catalytic reaction using methyl α-hydroxyisobutyrate as a raw material, in order to suppress hydrolysis of the ester group, methanol is supplied to a reactor with the amount thereof being 0.1 to 3.0 times by weight of methyl α-hydroxyisobutyrate to carry out the gas-phase catalytic reaction. In this regard, not only a dehydration reaction of the hydroxyl group of methyl α-hydroxyisobutyrate, but also a dehydration reaction of methanol occurs, causing by-production of dimethyl ether (hereinafter referred to as DME). Industrially, methanol is recovered in the purification process and reused, but when DME is by-produced, there are drawbacks that the methanol recovery ratio in the purification process is decreased, and that the production cost of methyl methacrylate is increased.

The present inventors made researches in order to improve the drawback, and found that the amount of by-produced DME varies depending on the type of a clay binder, and that in the case of a molded catalyst using bentonite, which belongs to the clay in which pH is less than 9 when dispersed in water described in Patent Document 6, the life is relatively long but the amount of by-produced DME is large and therefore the methanol recovery ratio is low, meanwhile in the case of a molded catalyst using synthetic hectorite, which belongs to the silica magnesia-based clay described in Patent Document 5, the amount of by-produced DME tends to be small and the methanol recovery ratio tends to be high but the life is short.

Specifically, the problem to be solved by the present invention is to provide a catalyst for use in the production of methyl methacrylate, which further suppresses by-production of DME caused by a dehydration reaction of methanol to prevent reduction in the methanol recovery ratio and has longer catalyst life in a method for producing methyl methacrylate by means of a gas-phase catalytic reaction using methyl α-hydroxyisobutyrate as a raw material compared to conventional methods, and a method for producing methyl methacrylate using the catalyst for use in the production of methyl methacrylate.

Means for Solving the Problems

The present inventors diligently made researches on the aforementioned problem, and found that, in a molded catalyst for use in the production of methyl methacrylate obtained by molding synthetic faujasite-type zeolite with use of a layered magnesium silicate compound as a binder, the sulfur content in the layered magnesium silicate compound affects the catalyst life in a methyl methacrylate synthesis reaction, and that when the sulfur content in the layered magnesium silicate compound is adjusted to be within a specific range or lower than that, the DME by-production ratio can be further suppressed to maintain a high methanol recovery ratio while providing a longer catalyst life when compared to conventional methods, and thus the present invention was achieved.

Specifically, the means for solving the problems of the present invention are as follows:

1. A molded catalyst for use in the production of methyl methacrylate, which comprises synthetic faujasite-type zeolite and a layered magnesium silicate compound, wherein the sulfur content in the layered magnesium silicate compound is 0.10% by weight or less.
2. The molded catalyst for use in the production of methyl methacrylate according to item 1, wherein the ratio of the layered magnesium silicate compound to the total of the synthetic faujasite-type zeolite and the layered magnesium silicate compound is 5 to 30% by weight.
3. The molded catalyst for use in the production of methyl methacrylate according to item 1 or 2, wherein the layered magnesium silicate compound is a synthetic layered magnesium silicate compound.
4. The molded catalyst for use in the production of methyl methacrylate according to item 3, wherein the synthetic layered magnesium silicate compound is a synthetic hectorite.
5. A method for producing methyl methacrylate, which comprises carrying out a gas-phase catalytic reaction of methyl α-hydroxyisobutyrate using the molded catalyst for use in the production of methyl methacrylate according to any one of items 1 to 4.
6. The method for producing methyl methacrylate according to item 5, wherein methanol is used as a diluent in an amount of 0.1 to 3.0 times by weight of methyl α-hydroxyisobutyrate.

Advantageous Effect of the Invention

According to the present invention, it is possible to provide a catalyst for use in the production of methyl methacrylate, which has a higher methanol recovery ratio and a longer catalyst life compared to those of conventional methods in a method for producing methyl methacrylate by means of a gas-phase catalytic reaction of methyl α-hydroxyisobutyrate as a raw material, and a method for producing methyl methacrylate using the catalyst for use in the production of methyl methacrylate.

EMBODIMENTS FOR CARRYING OUT THE INVENTION

Hereinafter, the present invention will be described in detail. The molded catalyst for use in the production of methyl methacrylate of the present invention comprises synthetic faujasite-type zeolite and a layered magnesium silicate compound. The synthetic faujasite-type zeolite of the present invention is an alumino silicate having a FAU-type crystal structure, "FAU" being a three-letter code representing a crystal structure of a crystalline molecular sieve defined by the International Zeolite Association (IZA). Regarding the type of the synthetic faujasite-type zeolite, generally known are the X type and the Y type, which have the same crystal structure but have a different chemical composition, i.e., a different atomic ratio of silicon/aluminium. Both the types can be suitably used. Among them, the transition type described in E. Dempsey, G. H. Kuhl, D. H. Olson, J. Phys. Chem., 73, 387 (1969) can be particularly suitably used. According to the document, a transition-type synthetic faujasite-type zeolite means a zeolite having a lattice constant, which is measured by X-ray diffraction, of 24.80 to 24.94 Å.

The cation type of the synthetic faujasite-type zeolite of the present invention is not particularly limited, but the sodium ion type is preferred, and it is particularly preferred that the atomic ratio of sodium to aluminium in zeolite (Na/Al atomic ratio) is 0.90 to 1.02. Further, the synthetic faujasite-type zeolite is generally produced by filtering, washing and drying a crystal obtained by hydrothermal synthesis under alkaline conditions. In this process, when washing is insufficient, an alkaline component remains in the crystal, and a zeolite in which the amount of free alkali is large as described below, which is defined in the aforementioned Patent Document 6, is obtained. The amount of free alkali in the synthetic faujasite-type zeolite to be used in the present invention is not particularly limited, but is preferably 0.1 milliequivalent or less per 1 g of zeolite.

The synthetic faujasite-type zeolite is produced in the form of fine powder unless it is produced as a molded binderless zeolite. In the case of industrial use as a fixed bed catalyst, it is difficult to use zeolite in the form of fine powder directly. For this reason, it is generally used in the form of a molded body having an appropriate shape such as a spherical shape and a column shape. However, since zeolite fine powder itself does not have mutual bonding capability, a binder is used for imparting appropriate plasticity and strength thereto. As such a binder, clay minerals such as kaolin and montmorillonite, or silica sol (colloidal silica), alumina sol, etc. are generally used. The binder for producing the molded catalyst for use in the production of methyl methacrylate of the present invention is not particularly limited as long as it is a magnesium-containing compound, but is preferably a layered magnesium silicate compound.

The layered magnesium silicate compound of the present invention is a compound having a layered crystalline structure composed of at least a silicon element, a magnesium element and an oxygen element. The layered magnesium silicate compound refers to a natural clay mineral existing in nature, a chemically synthesized product or a product obtained by modifying a natural clay mineral. The synthetic layered magnesium silicate compound refers to a chemically synthesized product or a product obtained by modifying a natural clay mineral. Examples of the synthetic layered magnesium silicate compound include a synthetic hectorite and a synthetic mica, which are chemically synthesized from a salt of sodium, lithium or magnesium and sodium silicate, and a modified hectorite and a modified mica, which are obtained by modifying a natural clay mineral. The layered magnesium silicate compound of the present invention is preferably a synthetic layered magnesium silicate compound, and among synthetic layered magnesium silicate compounds, a synthetic hectorite obtained by chemical synthesis is particularly preferred. The synthetic hectorite is a trioctahedral-type layered silicate having a smectite structure. In general, a salt of sodium, lithium or magnesium is mixed with sodium silicate to obtain a gel-like precipitate, it is subjected to hydrothermal synthesis in an autoclave to be converted into a layered silicate, and the obtained layered silicate is subjected to filtration and water washing or centrifugation and water washing, thereby obtaining the synthetic hectorite. The method for synthesizing a synthetic hectorite in the present invention is not particularly limited, and it is possible to use publicly-known methods, for example, the method for synthesizing hydrated magnesium silicate described in Japanese Laid-Open Patent Publication No. S49-135897, the method for producing a synthetic swellable silicate described in Japanese Laid-Open Patent Publication No. H06-345419, the method for producing a hectorite-like silicate described in Japanese Laid-Open Patent Publication No. H09-249412, and the method for producing synthetic magnesium silicate described in Japanese Laid-Open Patent Publication No. H11-71108. The type of the interlayer cation of the layered magnesium silicate compound in the present invention is not particularly limited, but the sodium ion type is preferred.

In the present invention, the sulfur content in the layered magnesium silicate compound is preferably 0.10% by weight or less. When the molded catalyst for use in the production of methyl methacrylate is obtained by molding the layered magnesium silicate compound having a sulfur content within the above-described range and synthetic faujasite-type zeolite, the molded catalyst exerts effects of suppressing by-production of DME in the methyl methacrylate synthesis reaction and maintaining a high methanol recovery ratio while providing a longer catalyst life. The sulfur content in the layered magnesium silicate compound is more preferably 0.09% by weight or less. For adjusting the sulfur content to 0.05% by weight or less, it is required to carry out washing with a large amount of water, and it may be impractical. For this reason, the sulfur content in the layered magnesium silicate compound is preferably 0.05% by weight or more.

Examples of methods for measuring the sulfur content in the layered magnesium silicate compound include publicly-known methods such as ICP atomic emission spectrophotometry (high-frequency inductively coupled plasma atomic emission spectrophotometry), ICP mass spectrometry (high-frequency inductively coupled plasma mass spectrometry) and fluorescent X-ray analysis. In the present application, the measurement was carried out by means of composition analysis of the layered magnesium silicate compound using fluorescent X-ray analysis (XRF method).

In the present application, the content (weight percentage) of each of silicon element, magnesium element, aluminium element, sodium element, sulfur element and oxygen element, and a slight amount of elements other than those in the layered magnesium silicate compound is measured by the XRF method. According to the measurement results, the ratio of sulfur to the total amount of 6 components, i.e., the silicon element, magnesium element, aluminium element, sodium element, sulfur element and oxygen element (excluding the slight amount of elements other than those) is regarded as the sulfur content in the layered magnesium silicate compound.

The reason why a molded catalyst for use in the production of methyl methacrylate which is molded by using a layered magnesium silicate compound having a low sulfur content has a long catalyst life has not been elucidated, but the present inventors consider the below-described matters. As described above, in the industrial production of the synthetic layered magnesium silicate compound, inexpensive sulfate or sulfuric acid is used as a raw material. In this case, sulfate ion is removed in the process of washing the synthetic layered magnesium silicate compound, but it is difficult to completely remove the sulfate ion, and it remains in the product as an impurity in the form of a salt such as sodium sulfate. Unlike the sodium ion existing in the layered crystal structure of the synthetic layered magnesium silicate, the sodium ion remaining in the form of a salt such as sodium sulfate acts as a free alkaline component in the production of methyl methacrylate by means of a dehydration reaction of methyl α-hydroxyisobutyrate in the present invention. For this reason, when a reaction is carried out using a molded catalyst having a high sulfur content, the amount of a high boiling point byproduct by-produced is large, and the catalyst life is short.

Regarding the ratio of the layered magnesium silicate compound in the molded catalyst for use in the production of methyl methacrylate of the present invention, the smaller the ratio of the layered magnesium silicate compound to the total weight of the synthetic faujasite-type zeolite and the layered magnesium silicate compound is, the longer the activity can be maintained, but the ratio is preferably 5 to 30% by weight because the catalytic activity can be maintained for a long period of time while holding the mechanical strength of the molded catalyst for use in the production of methyl methacrylate and in addition, it is easy to carry out molding. The ratio is more preferably 5 to 20% by weight, and particularly preferably 10 to 20% by weight.

The molded catalyst for use in the production of methyl methacrylate of the present invention may contain a molding aid and a lubricant for improving moldability. As the molding aid and the lubricant, for example, carboxymethyl cellulose, stearic acid, alcohols, surfactants, fibers, etc. can be used.

The magnesium content in the molded catalyst for use in the production of methyl methacrylate of the present invention is not particularly limited, but is preferably 0.5 to 6% by weight.

The sulfur content in the molded catalyst for use in the production of methyl methacrylate of the present invention is obtained by calculation based on the sulfur content in the layered magnesium silicate compound obtained by the above-described method and the content of the layered magnesium silicate compound in the molded body. The sulfur content in the molded catalyst for use in the production of methyl methacrylate of the present invention depends on the sulfur content in the layered magnesium silicate compound and the content of the layered magnesium silicate compound in the molded body, but is preferably 0.030% by weight or less, and more preferably 0.015% by weight or less.

The molded catalyst for use in the production of methyl methacrylate of the present invention can be produced by the below-described method, but there is no particular limitation thereon.

The method for producing a layered magnesium silicate compound having a sulfur content of 0.10% by weight or less is not particularly limited, but it is easily obtained by washing a publicly-known synthetic layered magnesium silicate compound, which is obtained by chemosynthesis or modification, with water at a high level. The method of water washing is not particularly limited, and general methods such as filtration and centrifugation can be used. The time of water washing can be suitably determined based on the method of water washing.

The molded catalyst for use in the production of methyl methacrylate of the present invention can be obtained by molding the synthetic faujasite-type zeolite and the layered magnesium silicate compound having a sulfur content of 0.10% by weight or less. The molding method is not particularly limited, and various methods including the extrusion molding method, tumbling granulation method and tablet molding method can be employed according to the shape of the molded body. Further, the shape of the molded body is not particularly limited, and for example, a spherical shape, a column shape, a ring shape, a petal shape, etc. can be employed.

Hereinafter, the method for producing methyl methacrylate of the present invention will be described. The method for producing methyl α-hydroxyisobutyrate as a raw material is not particularly limited, and it is possible to use methyl α-hydroxyisobutyrate produced by methanolysis of α-hydroxyisobutyric acid amide or amide-ester exchange of α-hydroxyisobutyric acid amide and methyl formate disclosed in Japanese Publication for Opposition No. H02-2874. Further, methyl α-hydroxyisobutyrate can also be obtained from a high boiling point byproduct obtained by the ACH process, in which methyl methacrylate is produced from acetone cyanhydrin and sulfuric acid, or the C4 direct oxidation process using isobutylene as a raw material. Methyl α-hydroxyisobutyrate recovered from such a high boiling point byproduct generally contains methyl α- or β-methoxyisobutyrate. The molded catalyst of the present invention is also effective for hydro-methoxy-elimination reaction of such homologues, and these can be recovered as methyl methacrylate.

The reaction of the present invention can be performed in the fixed bed gas-phase flow system, and a reactor of the heat insulation type, multi-tube heat exchange type or the like can be used. Methyl α-hydroxyisobutyrate as a raw material is preheated and vaporized, and then supplied to the reactor. The vaporized raw material can be directly introduced or introduced after diluted with an inert gas such as nitrogen, argon and helium. In order to improve the yield of methyl methacrylate, it is more preferred to use methanol as a diluent. The ratio of methanol as the diluent is preferably 0.1 to 3.0 times by weight, and particularly preferably 0.2 to 2.0 times by weight of methyl α-hydroxyisobutyrate. Regarding the supply rate of the raw material, the total weight of methyl α-hydroxyisobutyrate as the raw material and methanol as the diluent per unit catalyst weight, i.e., the weight hourly space velocity (WHSV) is preferably 0.1 to 5.0 hr$^{-1}$.

The reaction temperature is preferably 230 to 300° C. and may be held at a constant temperature. However, in order to suppress various byproducts and maintain the catalytic activity, it is more preferred to employ a method of slowly increasing the temperature within a specific temperature range over the reaction time so that the conversion of methyl α-hydroxyisobutyrate is maintained within the range of 98.0 to 99.9%. In this case, the initial reaction temperature is 230 to 270° C., and more preferably 240 to 260° C., and the final reaction temperature is 250 to 300° C., and more preferably 260 to 290° C. The adjustment of the reaction temperature in this way is required for compensation for the time-dependent decrease of active sites due to accumulation of a high boiling point byproduct, etc. to the catalyst. When it is no longer possible to maintain the conversion of methyl α-hydroxyisobutyrate within the range of 98.0 to 99.9% within the aforementioned reaction temperature range, the raw material supply is temporarily stopped, and the regeneration of the catalyst by burning the carbonaceous substances with air is carried out at a temperature at which the FAU-type structure of the catalyst is not destroyed, preferably not higher than 550° C., thereby recovering the catalytic activity almost completely. Thus, the molded catalyst of the present invention can be easily recovered and used repeatedly. The reaction pressure is not particularly limited, but the reaction can be performed under ordinary pressure or slightly elevated pressure.

The reaction product solution obtained by the method of the present invention contains unreacted raw materials and byproducts such as methacrylic acid, acetone and polymethylbenzenes in addition to methyl methacrylate as the objective substance. Such byproducts can be easily separated by applying thereto a usual purification method such as distillation and extraction.

EXAMPLES

Hereinafter, the present invention will be specifically described by way of examples, but the present invention is not limited thereto. The measurement of physical properties of the molded catalyst for use in the production of methyl methacrylate and the synthetic layered magnesium silicate compound of the present invention and the performance test of the molded catalyst for use in the production of methyl methacrylate in the methyl methacrylate synthesis reaction were carried out as described below.

Composition Analysis

The quantitative analysis of elements of silicon, magnesium, aluminium, sodium, sulfur and oxygen contained in the synthetic layered magnesium silicate compound was carried out by fluorescent X-ray analysis (XRF). A powder sample after dried at 150° C. was compression-molded into a plate-like shape, and it was measured using a scanning fluorescent X-ray analyzer ZSX Primas II manufactured by Rigaku Corporation. According to the above-described method, the content (weight percentage) of each of silicon element, magnesium element, aluminium element, sodium element, sulfur element and oxygen element, and a slight amount of elements other than those in the synthetic layered magnesium silicate compound is measured. According to the measurement results, the ratio of sulfur to the total amount of 6 components, i.e., the silicon element, magnesium element, aluminium element, sodium element, sulfur element and oxygen element (excluding the slight amount of elements other than those) was regarded as the sulfur content in the synthetic layered magnesium silicate compound.

pH Analysis

Regarding pH of the synthetic layered magnesium silicate compound, 2 wt % aqueous solution of the synthetic layered magnesium silicate compound was prepared, and it was subjected to the ultrasonic dispersion treatment and further left overnight to carry out complete dispersion, and the obtained solution was measured. The measurement was carried out using a pH meter D-54 manufactured by HORIBA, Ltd.

Performance Test in Methyl Methacrylate Synthesis Reaction

The performance test in the methyl methacrylate synthesis reaction was carried out using a fixed bed gas phase flow-type reaction apparatus equipped with a raw material tank, a raw material supply pump, a raw material gas introduction apparatus, a reaction tube (made of SUS316, inner diameter: 18 mmφ, length: 300 mm), a cooling apparatus, a reaction product solution collection apparatus, etc. In the performance test, 7 g of a molded catalyst subjected to particle size regulation to have a size of 10 to 20 mesh was put in the center of the reaction tube, a methanol solution containing 55 wt % of methyl α-hydroxyisobutyrate was supplied at 9 g/hr, and it was carried out under atmospheric pressure. The reaction temperature was gradually increased so that the conversion of methyl α-hydroxyisobutyrate was within the range of 99.5 to 99.9%, and the number of days until the reaction temperature reached 280° C. was regarded as the service life of the catalyst. Reaction results were derived from the data obtained by the quantitative analysis carried out by introducing the reaction product solution into a gas chromatograph analyzer.

In this regard, the methanol recovery ratio (MeOH recovery ratio), the dimethyl ether production ratio (DME production ratio) and the total yield of methyl methacrylate and methacrylic acid (MMA+MAA yield) were calculated as follows:

MeOH recovery ratio (%)=(mole number of methanol in reaction product solution)/(mole number of methanol in raw material)×100   (1)

DME production ratio (%)=(mole number of dimethyl ether in reaction product solution×2)/(mole number of methanol in raw material)×100   (2)

MMA+MAA yield (%)=(mole number of methyl methacrylate in reaction product solution+mole number of methacrylic acid in reaction product solution)/(mole number of methyl α-hydroxyisobutyrate in raw material)×100   (3)

Example 1

75.9 g of NaOH was dissolved in 462.9 g of ion-exchange water, and 27.7 g of sodium aluminate ($Al_2O_3$: 51.0 wt %, $Na_2O$: 36.0 wt %) was added thereto to be dissolved therein. In addition, a mixed solution of 333.0 g of silica sol ($SiO_2$: 20 wt %) and 200.0 g of ion-exchange water was added thereto, and it was stirred until it became a homogeneous slurry mixture. The above-described mixture was put into an autoclave to perform crystallization at 100° C. for 48 hours. After that, the temperature was lowered to room temperature, and it was filtered, washed with water until the amount of free alkali in the filtrate became 0.01 milliequivalent/g, and then dried at 150° C., thereby obtaining 51.6 g of white zeolite powder. When this zeolite was subjected to X-ray diffraction and chemical composition analysis, it was synthetic faujasite-type zeolite with a lattice constant of 24.86 Å and Na/Al=0.96.

Next, Laponite (registered trademark) RD, which is a synthetic hectorite commercially available from Rockwood Additives, was gelated with ion-exchange water, then it was put into a column, and ion-exchange water was flowed through the column from the top thereof to carry out washing. The obtained gel was dried using a drier at 90° C., and then crushed into powder using a mortar. The results of composition analysis of the binder (A) obtained according to the above-described method are shown in Table 1. The sulfur content in the binder (A) was 0.073 wt %.

17 g of the above-described synthetic faujasite-type zeolite powder was mixed with 3 g of Laponite RD powder in which the sulfur content was adjusted to 0.073 wt %, and further, ion-exchange water was gradually added thereto while kneading well, and after that, the mixture was molded, dried at 150° C. and burned at 350° C., thereby obtaining a molded catalyst. When composition analysis was carried out, the sulfur content in the obtained molded catalyst was 0.011 wt %, and the magnesium content was 2.67 wt %. When the aforementioned performance test in the methyl methacrylate synthesis reaction was carried out using the obtained molded catalyst, the service life of the catalyst was 65 days, the MeOH recovery ratio was 93.6%, the DME yield was 4.1%, and the MMA+MAA yield was 94.2%. Each of these reaction results is the average value during the reaction. The pH of the used Laponite RD was 10.15. The pH and reaction results are shown in Table 2.

Example 2

A catalyst was prepared in a manner similar to that in Example 1, except that a binder (B), which was obtained by washing Laponite RD to adjust the sulfur content to 0.062 wt %, was used instead of the binder (A) used in Example 1. The binder was subjected to composition analysis and pH measurement, and the performance test in the methyl methacrylate synthesis reaction was carried out. The pH and reaction results are shown in Table 2, and the results of composition analysis of the binder are shown in Table 1.

Comparative Example 1

A catalyst was prepared in a manner similar to that in Example 1, except that Laponite RD having a sulfur content of 0.114 wt % was used instead of the binder (A) used in Example 1. The binder was subjected to composition analysis and pH measurement, and the performance test in the methyl methacrylate synthesis reaction was carried out. The pH and reaction results are shown in Table 2, and the results of composition analysis of the binder are shown in Table 1.

Comparative Example 2

A catalyst was prepared in a manner similar to that in Example 1, except that Bengel 11 (manufactured by Nihon Yuukinendo Co., Ltd.) that is bentonite (silica aluminabased clay mineral) described in Patent Document 6 was used instead of Laponite RD. The pH was measured, and the performance test in the methyl methacrylate synthesis reaction was carried out. The pH and reaction results are shown in Table 2. Note that the sulfur content in the used Bengel 11 was 0.028 wt %.

According to these Examples and Comparative Examples, it is understood that the service lives of the catalysts described in Examples 1 and 2 are longer than that of the catalyst described in Comparative Example 1. Moreover, it is understood that the catalysts described in Examples 1 and 2 are excellent on the point that the service lives thereof are longer than that of the molded catalyst using bentonite of prior art (Comparative Example 2), and that the amount of loss of methanol calculated from the methanol recovery ratio is small.

TABLE 1

| | | Content of each element in binder (wt %) | | | | | |
|---|---|---|---|---|---|---|---|
| | Binder | O | Na | Mg | Al | Si | S |
| Example 1 | Binder (A) | 50.91 | 2.18 | 17.78 | 0.03 | 29.03 | 0.073 |
| Example 2 | Binder (B) | 51.66 | 1.97 | 18.00 | 0.03 | 28.28 | 0.062 |
| Comparative Example 1 | Laponite RD | 51.29 | 2.34 | 17.71 | 0.03 | 28.52 | 0.114 |

TABLE 2

| | Binder | pH | Catalyst life day | MeOH recovery ratio % | DME production ratio % | MMA + MAA yield % |
|---|---|---|---|---|---|---|
| Example 1 | Binder (A) | 10.15 | 65 | 93.6 | 4.1 | 94.2 |
| Example 2 | Binder (B) | 10.26 | 68 | 93.3 | 4.2 | 93.6 |
| Comparative Example 1 | Laponite RD | 10.16 | 42 | 93.5 | 4.1 | 92.6 |
| Comparative Example 2 | Bengel 11 | 8.49 | 56 | 92.7 | 5.4 | 92.1 |

The invention claimed is:

1. A molded catalyst for use in the production of methyl methacrylate, which comprises synthetic faujasite-type zeolite and a layered magnesium silicate compound, wherein the sulfur content in the layered magnesium silicate compound is 0.10% by weight or less.

2. The molded catalyst for use in the production of methyl methacrylate according to claim 1, wherein the ratio of the layered magnesium silicate compound to the total of the synthetic faujasite-type zeolite and the layered magnesium silicate compound is 5 to 30% by weight.

3. The molded catalyst for use in the production of methyl methacrylate according to claim 1, wherein the layered magnesium silicate compound is a synthetic layered magnesium silicate compound.

4. The molded catalyst for use in the production of methyl methacrylate according to claim 3, wherein the synthetic layered magnesium silicate compound is a synthetic hectorite.

5. A method for producing methyl methacrylate, which comprises carrying out a gas-phase catalytic reaction of methyl α-hydroxyisobutyrate using the molded catalyst for use in the production of methyl methacrylate according to claim 1.

6. The method for producing methyl methacrylate according to claim 5, wherein methanol is used as a diluent in an amount of 0.1 to 3.0 times by weight of methyl α-hydroxyisobutyrate.

* * * * *